United States Patent [19]
Anderson et al.

[11] 3,978,057
[45] *Aug. 31, 1976

[54] SUBSTITUTED AMINO-HYDRAZINOPYRIDAZINES

[75] Inventors: Paul L. Anderson, Dover; William J. Houlihan; Robert E. Manning, both of Mountain Lakes, all of N.J.

[73] Assignee: Sandoz, Inc., E. Hanover, N.J.

[ * ] Notice: The portion of the term of this patent subsequent to Aug. 10, 1988, has been disclaimed.

[22] Filed: May 2, 1974

[21] Appl. No.: 466,372

Related U.S. Application Data

[63] Continuation-in-part of Ser. No. 241,412, April 5, 1972, abandoned, which is a continuation-in-part of Ser. No. 40,727, May 26, 1970, abandoned, which is a continuation-in-part of Ser. No. 868,569, Oct. 22, 1969, abandoned, which is a continuation-in-part of Ser. Nos. 788,064, Dec. 30, 1968, abandoned, Ser. No. 845,043, July 25, 1969, abandoned, Ser. No. 847,471, Aug. 4, 1969, abandoned, and Ser. No. 860,048, Sept. 22, 1969, abandoned.

[52] U.S. Cl. .............................. 260/250 A; 424/250
[51] Int. Cl.² ....................................... C07D 237/20
[58] Field of Search ....................... 260/250 A, 250

[56] References Cited
UNITED STATES PATENTS

| 3,579,517 | 5/1971 | Houlihan et al. | 260/250 A |
| 3,598,822 | 8/1971 | Anderson et al. | 260/250 A |
| 3,622,671 | 11/1971 | Anderson et al. | 424/250 |
| 3,642,792 | 2/1972 | Bellasio et al. | 260/247.5 R |
| 3,706,744 | 12/1972 | Anderson et al. | 260/250 A |

OTHER PUBLICATIONS

Murakami et al., Journal of Heterocyclic Chemistry, 4(4), 555–563 (1967).

Primary Examiner—Alton D. Rollins
Assistant Examiner—Mark L. Berch
Attorney, Agent, or Firm—Gerald D. Sharkin; Robert S. Honor; Thomas O. McGovern

[57] ABSTRACT

Amino and substituted amino-hydrazinopyridazines, e.g., 4-methyl-amino-3-hydrazinopyridazine and 4-ethylamino-6-chloro-3-hydrazinopyridazine, are prepared from 3,4,6-trihalopyridazines and are active as hypotensive/antihypertensive agents.

16 Claims, No Drawings

SUBSTITUTED AMINO-HYDRAZINOPYRIDAZINES

This application is a continuation-in-part of U.S. patent application Ser. No. 241,412, filed Apr. 5, 1972, abandonded, which in turn is a continuation-in-part of application Ser. No. 40,727, filed May 26, 1970, now abandonded which in turn is a continuation-in-part of application Ser. No. 868,569, filed Oct. 22, 1969, now abandoned, which is a continuation-in-part of applications Ser. No. 788,064, filed Dec. 30, 1968, now abandoned; Ser. No. 845,043, filed July 25, 1969, now abandoned; Ser. No. 847,471, filed Aug. 4, 1969, now abandoned; and Ser. No. 860,048, filed Sept. 22, 1969, now abandoned.

This invention pertains to substituted hydrazinopyridazines which are useful as hypotensive/anti-hypertensive agents. Still more particularly, this invention concerns 4-and 5-amino and substituted amino-hydrazinopyridazines, intermediates and processes therefor, and acid addition salts thereof.

The novel compounds of this invention may be represented by the formula:

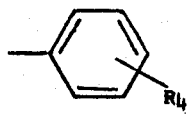

(I)

where
  $R_1$ represents hydrogen, lower alkyl, i.e., alkyl having 1 to 5 carbon atoms, such as methyl, ethyl, propyl, t-butyl, and the like; lower alkenyl, i.e., alkenyl having 3 to 5 carbon atoms such as allyl; —$(CH_2)_m OH$, wherein $m$ is 2, 3 or 4, such as hydroxyethyl, hydroxypropyl or hydroxybutyl; or

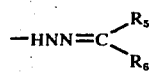

where
  $R_4$ represents hydrogen; halo having an atomic weight of about 19 to 36; lower alkyl as defined above; lower alkoxy, i.e., alkoxy having 1 to 5 carbon atoms such as methoxy, ethoxy, propoxy and the like or trifluoromethyl, and
one of
  $R_2$ and $R_3$ represents hydrazino or $$-HNN=C{<}^{R_5}_{R_6}$$

and the other represents hydrogen or halo having an atomic weight between about 35 to 80,
where
  $R_5$ and $R_6$ independently, represent hydrogen; lower alkyl; as defined above; lower alkenyl as defined above; styryl or

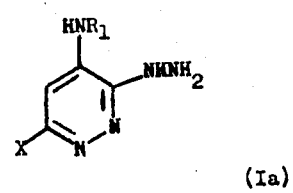

where $n$ is 0, 1, 2 or 3, provided that when one of $R_2$ or $R_3$ is hydrazino and the other is hydrogen, $R_1$ is other than hydrogen and that when one of $R_2$ or $R_3$ is hydrazino and the other is halo, $R_1$ is other than hydrogen or lower alkyl, and pharmaceutically acceptable acid addition salts thereof.

The compounds of formula (I) having the formula(Ia):

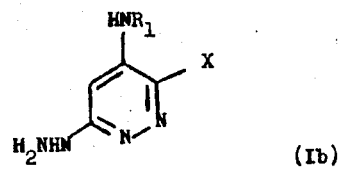

(Ia)

and (Ib):

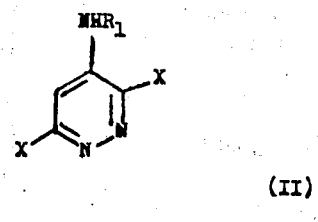

(Ib)

where
  X is halo of atomic weight between about 35 to 80 and
  $R_1$ and the proviso are as defined above
are prepared simultaneously by treating a compound of formula (II):

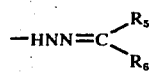

(II)

in which X, $R_1$ and the proviso are as defined above and each X is the same, with hydrazine.

Although the temperature is not critical, the reaction is suitably carried out at a temperature of about 20° to 115°C., preferably between about 60° to 115°C., and especially between about 80° to 115°C. The use of solvent is not necessary, although excess hydrazine or inert solvents such as lower alkanol, especially methanol or ethanol may be used if desired.

The resulting compounds of formula (Ia) and (Ib) may be recovered using conventional techniques, e.g., fractional crystallization, chromatography, and the like. The use of excess hydrazine sometimes facilitates separation of the co-products of the reaction as some of the compounds of formula (Ia) precipitate on cooling the reaction mixture. Compound (Ib) remains in solution and is isolated by conventional techniques. e.g., fractional precipitation using water as the diluent.

Compounds of formula (I) in which $R_2$ is hydrogen and $R_3$ is hydrazine are prepared according to the following reaction scheme:

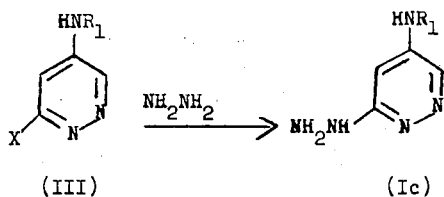

where X, $R_1$, and the proviso are as defined above.

Similarly, compounds of formula (I) in which $R_2$ is hydrazine and $R_3$ is hydrogen may be prepared according to the following reaction scheme:

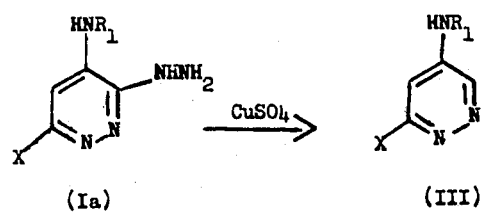

where X, $R_1$, and the proviso are as defined above.

The compounds (Ic) and (Id) are prepared by treating pyridazines (III) and (IV), respectively, with hydrazine. Although the temperature is not critical the reaction is generally carried out at about 20° to 115°C., preferably between about 60° to 115°C. and especially between about 80° to 115°C. Use of a solvent is not necessary, but excess hydrazine or inert solvents in particular lower alkanols, especially methanol or ethanol may be used if desired. The product (Ic) or (Id) is isolated by conventional techniques. e.g., fractional crystallization.

Compounds of formula (III) are prepared according to the following reaction scheme:

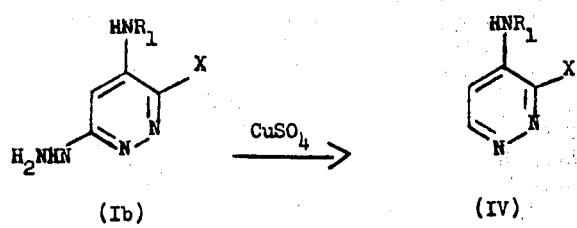

where X, $R_1$ and the proviso are as defined above.

Similarly, the compounds of formula (IV) are prepared according to the following reaction scheme:

where X, $R_1$ and the proviso are as defined previously.

The compounds of formula (III) and (IV) are prepared by treating the 3-hydrazinopyridazines (Ia) and (Ib) with copper sulfate at a temperature of 50° to 100°C. for 1 to 24 hours in an inert solvent, i.e., one which does not react with any of the reactants or the product. The temperature is not critical The preferred solvents are alcohol-water mixtures especially 1:1 alcohol-water where the alcohol has 1 to 5 carbon atoms. The products (III) and (IV) are isolated by conventional methods, e.g., crystallization.

The compounds of formula (I) in which $R_1$ is other than lower alkenyl and $R_2$ is hydrazine and $R_3$ is hydrogen can also be prepared from compound (Ia) according to the following reaction scheme:

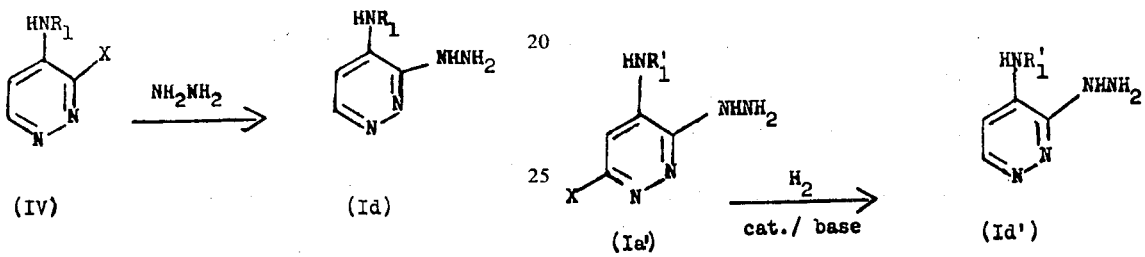

where X is as defined above and $R_1'$ has the same significance as $R_1$ except that it does not include hydrogen or lower alkenyl.

It will be understood that during the hydrogenation, the double bond of the alkenyl substituent is reduced thereby, transforming $R_1'$ into lower alkyl.

Similarly, the compounds of formula (I) in which $R_2$ is hydrogen, and $R_3$ is hydrazine, and $R_1$ is other than hydrogen or lower alkenyl are prepared from compound (Ib) according to the following reaction scheme:

where X, $R_1'$, and the proviso are as defined above.

The compounds (Ic') and (Id') may be prepared by hydrogenating compounds of formula (Ib') and (Ia') in the presence of a hydrogenation catalyst and alkali metal base in an inert solvent. The hydrogenation catalyst is preferably a platinum or palladium catalyst especially 5 to 10% platinum or palladium on carbon. The preferred alkali metal bases are sodium hydroxide and potassium hydroxide. The inert solvents preferred are the lower alcohols, especially methanol, ethanol, or isopropyl alcohol; aromatic solvents, particularly benzene and toluene, and ethers, especially tetrahydrofuran. The temperature of the reaction and the pressure of the hydrogen are not critical in the hydrogenation. The process can be carried out at a temperature of about 0° to 50°C., preferably 20° to 30°C., especially between 20° and 25°C. The hydrogenation is carried out preferably at pressures which vary from about 14 psi (about 1 atmosphere) to about 50 psi. Compounds (Ic') and (Id') are recovered by conventional techniques, e.g., by evaporation and recrystallization or by salt formation and precipitation.

The compound of formula (I) in which $R_2$ is

where $R_5$ and $R_6$ are as defined previously may be prepared according to the following reaction scheme:

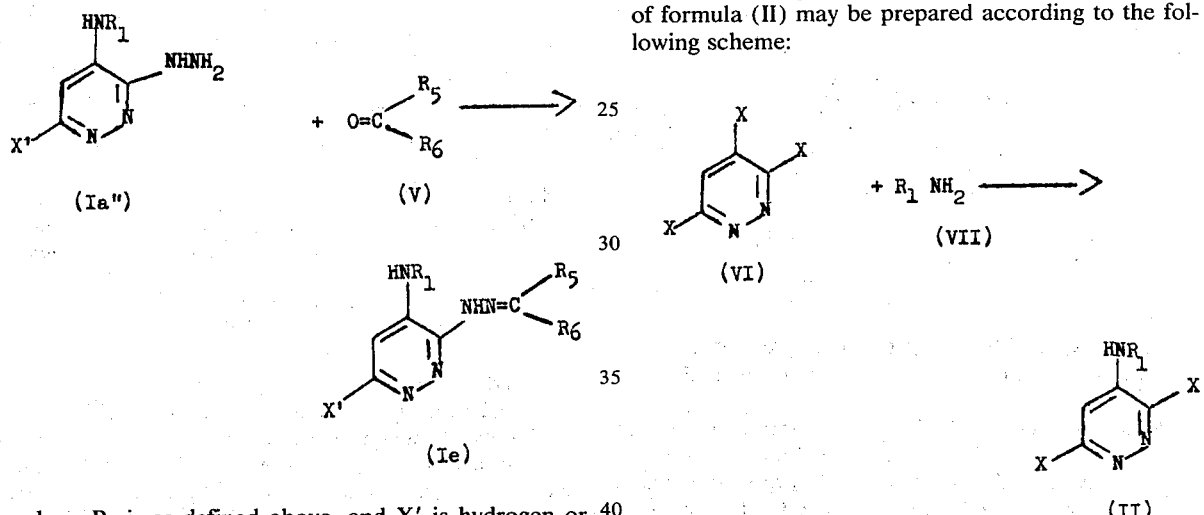

where $R_1$ is as defined above, and X' is hydrogen or halo of atomic weight between about 35 to 80.

Similarly, the compound of formula (I) in which $R_3$ is

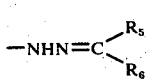

where $R_5$ and $R_6$ are as defined above may be prepared according to the following reaction scheme:

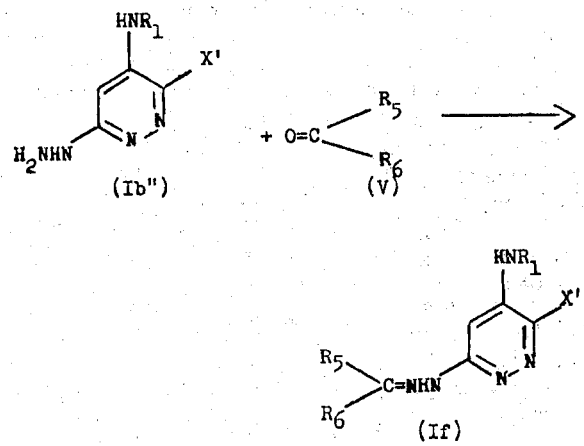

where $R_1$ and X' are as previously defined.

The hydrazones (Ie) and (If) are prepared by treating hydrazinopyridazines of the formula (Ia'') and (Ib'') with a carbonyl compound (V). Although a solvent is not necessary, the reaction is generally carried out in excess carbonyl compound (V) or in an inert solvent, i.e., one which is non-reactive with the reactants or product. The preferred solvents are lower alkanols, especially methanol or ethanol. The reaction is normally carried out at temperatures between 20°C. and 80°C., preferably 20° to 30°C. The product is recovered by conventional techniques, e.g., by the addition of water to precipitate the product or by concentration of the reaction mixture thereby causing the product to precipitate.

The compounds of formula (II), where the substituent $R_1$ as defined above is other than hydrogen or lower alkyl and their acid addition salts are new and represent an additional aspect of this invention. The compounds of formula (II) may be prepared according to the following scheme:

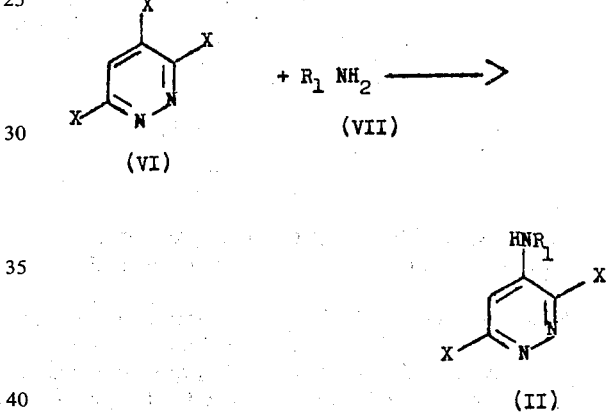

where X and $R_1$ are as defined above, and each X is the same.

The pyridazines (II) are prepared by treating 3, 4, 6-trihalo pyridazine (VI) with an appropriate amine (VII). Although the temperature is not critical, the reaction is normally carried out at a temperature between about 0° to 100°C., preferably between about 20° to 80°C., more preferably 20° to 30°c. Although not necessary, inert solvent may be used, preferably lower alkanols, especially methanol, ethanol and isopropanol. When feasible, excess reactant (VII) may also be used as solvent. The compounds (II) are recovered using conventional techniques, e.g., evaporation or crystallization.

The compounds of formula (II) in which $R_1$ is hydrogen or lower alkyl are known and can be prepared by methods described in the literature or disclosed herein. The pyridazines of formula (VI) and many of the pyridazines, carbonyl compounds and amines of formulae (III), (IV), (V), and (VII) are known and are prepared according to methods disclosed in literature. The pyridazines (III) and (IV), carbonyls (V) and amines (VII) which are not known can be prepared by analogous methods or by methods herein described from known materials.

The compounds of formula (I) in which $R_1$ is lower alkyl, when one of $R_2$ and $R_3$ is hydrazino and the other is hydrogen, or lower alkenyl are of interest; and the compounds of formula (I) having the structure:

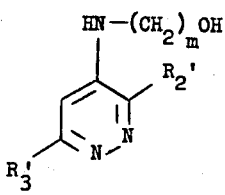

(Ig)

where
m is 2, 3 or 4, and
one of $R_2'$ is hydrazino and the other is hydrogen or halo of atomic weight between 35 to 80 and pharmaceutically acceptable acid addition salts thereof
are particularly interesting.

Also of interest are the compounds of formula (I) having the structure

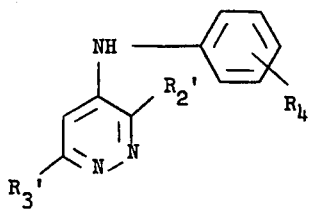

(Ih)

where
one of $R_2'$ and $R_3'$ is hydrazino and the other is hydrogen or halo of atomic weight between 35 to 80, and
$R_4$ is hydrogen; halo having an atomic weight of about 19 to 36; lower alkyl as defined above; lower alkoxy, i.e., alkoxy having 1 to 5 carbon atoms such as methoxy, ethoxy, propoxy, and the like or trifluoromethyl, and
pharmaceutically acceptable acid addition salts thereof.

The hydrazones of interest are those having the structure

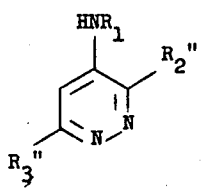

(Ii)

where
one of $R_2''$ and $R_3''$ is hydrogen or halo having an atomic weight of 35 to 80 and the other is

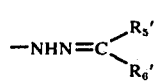

where
$R_5'$ and $R_6'$ each independently represent hydrogen, lower alkyl or lower alkenyl, and
$R_1$ is as defined above, and pharmaceutically acceptable acid addition salts thereof.

The compounds of formula (I) in which one or both of $R_5$ and $R_6$ are styryl are also of interest, and of particular interest are the compounds of formula (I) having the structure

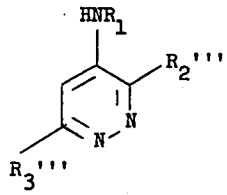

(Ij)

where
one of $R_2'''$ and $R_3'''$ is hydrogen or halo having an atomic weight of 35 to 80 and the other is

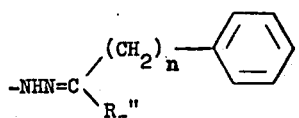

(Ik)

where
$R_5''$ is hydrogen, lower alkyl, lower alkenyl or

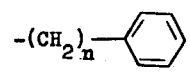 and $n$ and $R_1$ are as defined above, and
pharmaceutically acceptable acid addition salts.

The pyridazines represented by formula (I), including those in which $R_1$ is a lower alkyl of 2 to 5 carbon atoms when one of $R_2$ or $R_3$ is hydrazino, are useful because they possess pharmacological activity in animals. These compounds are useful, in particular, as hypotensive/anti-hypertensive agents, as indicated by their activity in renal hypertensive rats given 30, 10 and 3 mg/kg of active compound using the technique of A. Grollman (Proc. Soc. Exptl. Biol. and Med. 57: 102, 1944) and indirectly measuring the blood pressure from the caudal artery in the tail using a pneumatic pulse transducer.

Compounds of formula (I), in which $R_1$ is alkenyl of 3 to 5 carbon atoms as previously indicated, in particular, 4-allylamino-6-chloro-3-hydrazinopyridazine and 4-methallylamino-6-chloro-3-hydrazinopyridazine and also 4-anilino-6-chloro-3-hydrazinopyridazine, are also useful as anti-inflammatory agents as indicated by their activity in rats given 25 mg/kg of active compound orally and tested using the acute carrageenan-induced edema procedure substantially as described by Winter (Proc. Soc. Exptl. Biol., 111: 544, 1962).

When so utilized, the compounds may be combined with one or more pharmaceutically acceptable carriers or adjuvants. They may be administered orally or parenterally and, depending upon the compound employed and the mode of administration, the exact dosage utilized may vary.

Furthermore, the compounds (I) may be similarly administered in the form of their non-toxic pharmaceutically acceptable acid addition salts. Such salts possess the same order of activity as the free base, are readily prepared by reacting the base with an appropriate acid and, accordingly, are included within the scope of the invention. Representative of such salts are the mineral acid salts, such as the hydrochloride, hydrobromide, sulfate, phosphate and the like and the oroganic acid salts, such as the succinate, benzoate, acetate, p-toluenesulfonate, benzenesulfonate, and the like.

In general, satisfactory results are obtained when these compounds are administered as a hypotensive/antihypertensive agent at a daily dosage of about 0.2 milligrams to about 100 milligrams per kilogram of animal body weight. This daily dosage is preferably administered 2 to 4 times a day, or in sustained release form. For most large mammals, such as primates, the total daily dosage is from about 15 milligrams to about 600 milligrams. Dosage forms suitable for internal use comprise from about 3.5 milligrams to about 300 milligrams of the active compound in intimate admixture with a solid or liquid pharmaceutically acceptable carrier or diluent.

When a compound of formula I, in particular, the aforementioned compounds 4-allylamino-6-chloro-3-hydrazinopyridazine, 4-methallylamino-6-chloro-3-hydrazinopyridazine, or 4-anilino-6-chloro-3-hydrazinopyridazine, is used as an anti-inflammatory agent, satisfactory results are obtained at a daily dosage of about 0.4 milligrams to about 100 milligrams per kilogram of animal body weight. This daily dosage is preferably administered 2 to 4 times a day, or in sustained release form. For most large animals, such as primates, the total daily dosage is from about 30 milligrams to 600 milligrams. Dosage forms suitable for internal use comprise from about 7.5 milligrams to about 300 milligrams of the active compound in intimate admixture with a solid or liquid pharmaceutically acceptable carrier or diluent.

Tablets and Capsules Suitable For Oral Administration

Tablets and capsules containing the ingredients indicated below may be prepared by conventional techniques and are useful in treating hypertension at a dose of one tablet or capsule 2 to 4 times a day.

| Ingredient | Weight (mg) tablet | capsule |
|---|---|---|
| 4-ethylamino-6-chloro-3-hydrazino pyridazine | 10 | 10 |
| tragacanth | 10 | — |
| lactose | 237.5 | 290 |
| corn starch | 25 | |
| talcum | 15 | |
| magnesium stearate | 2.5 | |
| Total | 300 mg. | 300 mg. |

Sterile Suspension For Injection and Oral Liquid Suspension

The following pharmaceutical compositions are formulated with the indicated amount of active agent using conventional techniques. The injectable suspension and the oral liquid suspension represent formulations useful as unit doses and may be administered in the treatment of hypertension. The injectable suspension is suitable for administration once a day whereas the oral liquid suspension is suitably administered 2 to 4 times a day for this purpose.

| Ingredients | Weight (mg) sterile injectable suspension | oral liquid suspension |
|---|---|---|
| active agent | 50 | 25 |
| sodium carboxy methylcellulose U.S.P. | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.g. Tween 80), USP | — | 5 |
| sorbitol solution, 70%, U.S.P. | — | 2,500 |
| buffer agent to adjust pH for desired stability | q.s. | q.s. |
| water | q.s. for injection q.s. to 1 ml. | q.s. to 5 ml. |

EXAMPLE 1

3,6-dichloro-4-ethylaminopyridazine

To a stirred ice bath cooled solution of 70.0 g of 3,4,6-trichloropyridazine in 300 ml of ethanol is added dropwise 109 ml of 70% ethylamine solution. The reaction mixture is then allowed to warm to room temperature and stirred for an additional 2 hours. Most of the solvent is removed at room temperature, and to the mixture, is added 50 ml of water. The solid 3,6-dichloro-4-ethylamino pyridazine is collected by filtration. Second and third crops are collected after evaporation of additional ethanol; m.p. 97° to 99°C.

When isopropylamino or n-butylamine is used in place of ethylamine in the above process, 3,6-dichloro-4-isopropylamine pyridazine (m.p. 52°–54°C) or 3,6-dichloro-4-n-butylamino pyridazine (m.p. 52°–54°C), respectively, is obtained.

EXAMPLE 2

3,6-dichloro-4-(2-hydroxyethylamino)pyridazine

To a stirred icebath cooled solution of 55 g of 3,4,6-trichloropyridazine in 250 ml of ethanol is added 83 ml of ethanolamine. The reaction mixture is stirred for 1 hour. The product, 3,6-dichloro-4-(2-hydroxyethylamino) pyridazine (M.P. 146° to 146.5°C.) which separates, is collected by filtration.

EXAMPLE 3

3,6-dichloro-4-allylamino pyridazine

To a stirred solution of 91.7 g of 3,4,6-trichloropyridazine in 1000 ml of ethanol is added slowly with cooling 85.9 g of allylamine. After stirring 2 hours at room temperature, the mixture is cooled and the resultant precipitate 3,6-dichloro-4-allylamino pyridazine is collected by filtration. Concentration of the filtrate to 200 ml gives a second crop and concentration to 100 ml gives a third crop; m.p. 95° to 98°C.

EXAMPLE 4

3,6-dichloro-4-methallylamino pyridazine

To a stirred solution of 46.6 g of 3,4,6-trichloropyridazine in 250 ml of ethanol cooled by an ice bath is added dropwise 28.6 g of methallylamine. The reaction mixture is refluxed for 71 hours and the solvent removed at room temperature by vacuum evaporation. The product obtained is 3.6-dichloro-4-methallylamino pyridazine; m.p. 172° to 175°C.

EXAMPLE 5

3,6-dichloro-4-anilino pyridazine

To a stirred solution of 25.0 g. of 3,4,6-trichloropyridazine in 100 ml of ethanol is added 58 g of aniline. After stirring for 72 hours at 25°C., the solvent is partially removed under vacuum. The product obtained is 3,6-dichloro-4-anilino pyridazine; m.p. 137°–139°C.

When the above process is carried out and p-chloroaniline, p-ethylaniline, p-methoxyaniline or $\alpha,\alpha,\alpha$-trifluoro-p-toluidine is used in place of aniline, 3,6-dichloro-4-(p-chloroanilino)pyridazine, 3,6-dichloro-4-(p-ethylanilino)pyridazine, 3,6-dichloro-4-(p-methoxyanilino) pyridazine, or 3,6-dichloro-4-($\alpha,\alpha,\alpha$-trifluoro-p-toluidino) pyridazine, respectively is obtained.

EXAMPLE 6

4-ethylamino-6-chloro-3-hydrazino pyridazine

To 47.0 g. of 3,6-dichloro-4-ethylamino pyridazine is added slowly with stirring 550 g. of a 97% hydrazine solution. The mixture is refluxed for 1 hour and cooled; and the precipitate, 4-ethylamino-6-chloro-3-hydrazino pyridazine is collected. Further cooling gives a second crop; m.p. 177° to 179°C.

When 3,6-dichloro-4-isopropylamino pyridazine is substituted for 3,6-dichloro-4-ethylamino pyridazine in the above process, 4-isopropylamino-6-chloro-3-hydrazino pyridazine (m.p. 132° to 135°C) is obtained.

The 4-ethylamino-6-chloro-3-hydrazino pyridazine above is dissolved in methanol, and hydrogen chloride gas is bubbled through the solution at room temperature for about one-half hour. The product, 4-ethylamino-6-chloro-3-hydrazino pyridazine dihydrochloride (m.p. 225° to 227°C), precipitates and is collected by filtration.

When 4-isopropylamino-6-chloro-3-hydrazino pyridazine is substituted for 4-ethylamino-6-chloro-3-hydrazino pyridazine in the preceeding process, 4-isopropylamino-6-chloro-3-hydrazino pyridazine dihydrochloride (m.p. 209° to 212°C.) is obtained.

EXAMPLE 7

4-(2-hydroxyethylamino)-6-chloro-3-hydrazino pyridazine

To 40 g of 3,6-dichloro-4-(2-hydroxyethylamino)-pyridazine is added slowly with stirring 430 g of 97% hydrazine. The mixture is stirred for 20 hours and cooled. Water is added, and the precipitate, 4-(2-hydroxyethylamino)-6-chloro-3-hydrazino pyridazine (m.p. 168° to 172°C.), is collected by filtration.

The free base is dissolved in methanol and hydrogen chloride gas is bubbled through at room temperature for about 30 minutes. The product, 4-(2-hydroxyethylamino)-6-chloro-3-hydrazino pyridazine dihydrochloride (m.p. 204° to 208°C.), precipitates upon removal of part of the solvent and is collected by filtration.

EXAMPLE 8

4-Allylamino-6-chloro-3-hydrazino pyridazine

To 30.5 g of 4-allylamino-3,-dichloropyridazine is added with stirring 150 ml of a 97% hydrazine solution. The mixture is refluxed for 3 hours, then cooled and the precipitate collected by filtration. Further cooling gives a second crop. Recrystallization from methanol yields 4-allylamino-6-chloro-3-hydrazino pyridazine; m.p. 184°–186°C.

When the free base is treated with hydrogen chloride gas in the manner described in Examples 6 and 7, the product obtained is 4-allylamino-6-chloro-3-hydrazino pyridazine dihydrochloride; m.p. 199° to 202°C.

EXAMPLE 9

4-methallylamino-6-chloro-3-hydrazino pyridazine

To 32.0 g of 3,6-dichloro-4-methallylamino pyridazine is added slowly with stirring 232 ml of 97% hydrazine solution. The mixture is stirred overnight at 60°C. and then cooled to about 0°C, whereupon the 4-methallylamino-6-chloro-3-hydrazino pyridazine (m.p. 171° to 173°C.) precipitates and is collected by filtration.

EXAMPLE 10

4-anilino-6-chloro-3-hydrazine pyridazine

To 6.8 g of 3,6-dichloro-4-anilinopyridazine is added slowly with stirring 63 ml of 97% hydrazine. The mixture is stirred for 3 hours at 100°C. and then cooled, whereupon 4-anilino-6-chloro-3-hydrazine pyridazine (m.p. 169° – 171°C.) precipitates and is collected. The free base is dissolved in methanol, and hydrogen chloride gas is bubbled through the solution for about 30 minutes at room temperature. The product obtained is 4-anilino-6-chloro-3-hydrazino pyridazine dihydrochloride, m.p. 223° to 225°C.

When 3,6-dichloro-4-(p-chloroanilino)pyridazine, 3,6-dichloro-4-(p-ethylanilino)pyridazine, 3,6-dichloro-4-(p-methoxyanilino)pyridazine or 3,6-dichloro-4-($\alpha,\alpha,\alpha$-trifluoro-p-toluidino)pyridazine is used in place of 3,6-dichloro-4-anilinopyridazine in the process above, the free base obtained is 4-(p-chloroanilino)-6-chloro-3-hydrazino pyridazine, 4-(p-ethylanilino)-6-chloro-3-hydrazino pyridazine, 4-p-methoxyanilino-6-chloro-3-hydrazino pyridazine, or 4-($\alpha,\alpha,\alpha$-trifluoro-p-toluidino)-6-chloro-3-hydrazino pyridazine, respectively.

EXAMPLE 11

4-(n-butylamino)-6-chloro-3-hydrazino pyridazine

To 53 g. of 3,6-dichloro-4-butylamino-pyridazine is added slowly with stirring 523 ml. of 97% hydrazine solution. The mixture is stirred overnight at room temperature and then cooled to about 0°C., whereupon the 4-(n-butylamino)-6-chloro-3-hydrazino-pyridazine precipitates, m.p. 170° to 172°C.

The free base is dissolved in methanol and hydrogen chloride gas is bubbled through the solution at room temperature for about one-half hour. The product 4-n-butylamino-6-chloro-3-hydrazinopyridazine dihydrochloride (m.p. 178° to 180°C.) precipitates and is collected by filtration.

EXAMPLE 12

4-butylamino-3-chloro-6-hydrazino-pyridazine dihydrochloride

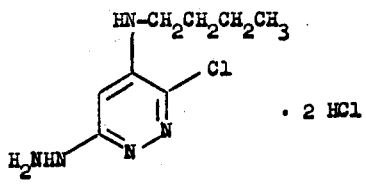

After removing the precipitated 4-(n-butylamino)-6-chloro-3-hydrazinopyridazine in Example 11 and washing with a small amount of water, the wash water is added to the filtrate to precipitate any residual 4-(n-butylamino)-6-chloro-3-hydrazinopyridazine remaining in the filtrate. The second precipitate is removed and additional water is then added to precipitate 4-butylamino-3-chloro-6-hydrazinopyridazine (m.p. 112°–116°C.)

The free base is dissolved in methanol and treated with hydrogen chloride gas for 35 minutes at room temperature. The majority of the methanol is removed by evaporation and the product, 4-butylamino-3-chloro-6-hydrazinopyridazine dihydrochloride, m.p. 131°–134°C., is precipitated by adding a small amount of ether.

When the filtrate from the preparation of 4-amino-6-chloro-3-hydrazinopyridazine, 4-methylamino-6-chloro-3-hydrazinopyridazine, 4-ethylamino-6-chloro-3-hydrazinopyridazine, 4-isopropylamino-6-chloro-3-hydrazinopyridazine, 4-(2-hydroxyethylamino)-6-chloro-3-hydrazinopyridazine, 4-allylamino-6-chloro-3-hydrazinopyridazine, 4-methallylamino-6-chloro-3-hydrazinopyridaine, 4-anilino-6-chloro-3-hydrazinopyridazine, 4-(p-toluidino)-6-chloro-3-hydrazinopyridazine, 4-(p-chlorophenylamino)-6-chloro-3-hydrazinopyridazine, 4-(p-methoxyphenylamino)-6-chloro-3-hydrazinopyridazine, or 4-($\alpha,\alpha,\alpha$-trifluoro-p-toluidino)-6-chloro-3-hydrazinopyridazine is used in place of the filtrate from the preparation of 4-(n-butylamino)-6-chloro-3-hydrazinopyridazine in the process of this example, 4-amino-3-chloro-6-hydrazinopyridazine, 4-methylamino-3-chloro-6-hydrazinopyridazine, 4-ethylamino-3-chloro-6-hydrazinopyridazine, 4-isopropylamino-3-chloro-6-hydrazinopyridazine, 4-(2-hydroxyethylamino)-3-chloro-6-hydrazinopyridazine, 4-allylamino-3-chloro-6-hydrazinopyridazine, 4-methallylamino-3-chloro-6-hydrazinopyridazine, 4-anilino-3-chloro-6-hydrazinopyridazine, 4-(p-toluidino)-3-chloro-6-hydrazinopyridazine, 4-(p-chlorophenylamino)-3-chloro-6-hydrazinopyridazine, 4-(p-methoxyphenylamino)-3-chloro-6-hydrazinopyridazine or 4-($\alpha,\alpha,\alpha$-trifluoro-p-toluidino)-3-chloro-6-hydrazinopyridazine, respectively, is obtained.

EXAMPLE 13

4-amino-3-hydrazinopyridazine

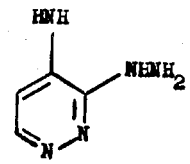

A solution of 4 g of 4-amino-6-chloro-3-hydrazinopyridazine in 240 ml. of methanol and 60 ml. of 0.5 N sodium hydroxide in methanol are charged into a Paar shaker. To this solutionn, 2 g. of 10% palladium on carbon catalyst is added. The Paar shaker is charged at room temperature with hydrogen to an initial pressure of 50 psi and shaken. After about 4 hours, the reaction mixture is filtered, the solvent evaporated, and the residue extracted with chloroform. The chloroform solution is evaporated to dryness, and the 4-amino-3-hydrazino pyridazine obtained is dissolved in methanol. Hydrogen chloride gas is bubbled in, and the 4-amino-3-hydrazinopyridazine dihydrochloride (m.p. 281°–283°C.) which precipitates is separated by filtration.

When 4-amino-3-chloro-6-hydrazinopyridazine is used in place of 4-amino-6-chloro-3-hydrazinopyridazine in the process of the example, 5-amino-3-hydrazinopyridazine dihydrochloride is obtained.

EXAMPLE 14

4-methylamino-3-hydrazinopyridazine

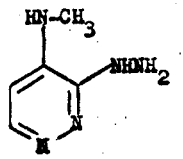

A solution of 10 g. of 4-methylamino-6-chloro-3-hydrazinopyridazine in 450 ml. of methanol and 150 ml. of 0.5 N sodium hydroxide in methanol are charged into a Paar shaker. To this solution, 2 g. of 10% palladium on carbon is added. The Paar shaker is charged with hydrogen at room temperature to an initial pressure of 50 psi and shaken. After about 6.5 hours, the reaction mixture is filtered, the solvent evaporated and the residue extracted with chloroform. The chloroform solution is evaporated to dryness and the 4-methylamino-3-hydrazinopyridazine obtained is dissolved in methanol. Hydrogen chloride gas is bubbled in, and the 4-methylamino-3-hydrazinopyridazine dihydrochloride (m.p. 247°–251°C.) which precipitates is collected by filtration.

EXAMPLE 15

4-isobutylamino-3-hydrazinopyridazine

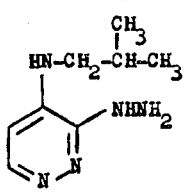

A solution of 4.0 of 4-methallylamino-6-chloro-3-hydrazinopyridazine in 150 ml. of methanol and 50 ml. of 0.5 N sodium hydroxide in methanol are charged into a Paar shaker. To this solution 2.0 g. of 10% palladium on carbon is added. The Paar shaker is charged with hydrogen at room temperature to an initial pressure of 50 psi and shaken. After about 4 hours, the reaction mixture is filtered, the solvent evaporated and the residue extracted with chloroform. The chloroform is evaporated off and the 4-isobutylamino-3-hydrazinopyridazine obtained is dissolved in methanol. Hydrogen chloride gas is bubbled in, and the product, 4-isobutylamino-3-hydrazinopyridazine hydrochloride (m.p. 211°–212°C.) which precipitates, is collected by filtration.

When 4-ethylamino-6-chloro-3-hydrazinopyridazine, 4-isopropylamino-6-chloro-3-hydrazinopyridazine, 4-allylamino-6-chloro-3-hydrazino pyridazine, 4-amilino-6-chloro-3-hydrazinopyridazine, 4-(p-ethylanilino)-6-chloro-3-hydrazinopyridazine, 4-(p-methoxyanilino)-6-chloro-3-hydrazinopyridazine, or 4-(α,α,α-trifluoro-p-toluidino)-6-chloro-3-hydrazinopyridazine is used in place of the 4-methallylamino-6-chloro-3-hydrazinopyridazine above, 4-ethylamino-3-hydrazinopyridazine, 4-isopropylamino-3-hydrazinopyridazine, 4-(n-propylamino)-3-hydrazinopyridazine, 4-anilino-3-hydrazinopyridazine, 4-(p-ethylanilino)-3-hydrazinopyridazine, 4-(p-methoxyanilino)-3-hydrazinopyridazine or 4-(α,α,α-trifluoro-p-toluidino)-3-hydrazinopyridazine, respectively, is obtained.

EXAMPLE 16

5-amino-3-hydrazinopyridazine

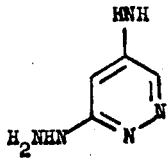

a. 3-chloro-5-aminopyridazine

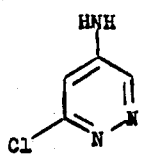

Into a 5 liter flask equipped with a heating mantle and stirrer are charged under nitrogen 50 g. of 4-amino-6-chloro-3-hydrazinopyridazine, 1500 ml. of water and 1000 ml. of methanol. The mixture is heated to 70°C. and stirred until dissolution takes place. To this solution is added slowly 237 g. of CuSO$_4$·5H$_2$O dissolved in 1000 ml. of water. The reactants are refluxed for 3 hours at 85°C. The pH of the solution is adjusted to 8.0 with 2N sodium hydroxide and the reaction mixture is filtered to remove copper oxide. The pH of the filtrate is readjusted to 4 with glacial acetic acid and evaporated to dryness.

The crude product is dissolved in 750 ml. of methanol and 750 ml. of water by heating to 60°C. The pH of the solution is adjusted to about 11 with 2N NaOH and the solution is filtered to remove residual copper oxide. The pH of the filtrate is reduced to about 4 with glacial acetic acid and the solvent is removed by evaporation. The residue is extracted with 200, 200, and 100 ml. portions of acetone, which are combined and filtered to remove sodium acetate. The acetone is removed by evaporation and the residue recrystallized from methanol. The product is 3-chloro-5-aminopyridazine; m.p. 153°–156°C.

b. 5-amino-3-hydrazinopyridazine

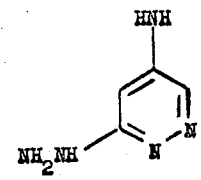

7 g. of 3-chloro-5-aminopyridazine is added to 125 ml. of hydrazine and the mixture is stirred under nitrogen for 17.5 hours at a temperature below reflux. The reaction mixture is cooled to room temperature, and the residual hydrazine removed by evaporation. The residue is treated with 250 ml. of methanol to extract the product. After separating the extractant and washing the residue with small amounts of methanol, the combined extractant-filtrate is treated with hydrogen chloride gas. The solution is then treated with ether to give a crystalline product which is recrystallized from methanol to give 5-amino-3-hydrazinopyridazine dihydrochloride; m.p. 220°–222°C.

When 4-methylamino-6-chloro-3-hydrazinopyridazine, 4-ethylamino-6-chloro-3-hydrazinopyridazine, 4-isopropylamino-6-chloro-3-hydrazinopyridazine, 4-n-butylamino-6-chloro-3-hydrazinopyridazine, 4-(2-hydroxyethylamino)-6-chloro-3-hydrazinopyridazine, 4-allylamino-6-chloro-3-hydrazinnopyridazine, 4-methallylamino-6-chloro-3-hydrazinopyridazine, 4-anilino-6-chloro-3-hydrazinopyridazine, 4-(p-chloroanilino)-6-chloro-3-hydrazinopyridazine, 4-(p-chloroanilino)-3-chloro-6-hydrazinopyridazine, 4-(p-ethylanilino)-6-chloro-3-hydrazinopyridazine, 4-(p-methoxyanilino)-6-chloro-3-hydrazinopyridazine, or 4-(α,α,α-trifluoro-p-toluidino)-6-chloro-3-hydrazinopyridazine is substituted for 4-amino-6-chloro-3-hydrazinopyridazine in the process of this example, the free base obtained is 5-methylamino-3-hydrazinopyridazine, 5-ethylamino-3-hydrazinopyridazine, 5-isopropylamino-3-hydrazinopyridazine, 5-n-butylamino-3-hydrazinopyridazine, 5-(2-hydroxyethylamino)-3-hydrazinopyridazine, 5-allylamino-3-hydrazinopyridazine, 5-methallylamino-3-hydrazinopyridazine, 5-anilino-3-hydrazinopyridazine, 5-(p-chloroanilino)-3-hydrazinopyridazine, 4-(p- chloroanilino)-3-hydrazinopyridazine, 5(p-ethylanilino)-3-hydrazinopyridazine, 5-(p-methoxyanilino)-3-hydrazinopyridazine, or 5-(α,α,α-trifluoro-p-toluidino)-3-hydrazinopyridazine, respectively.

Example 17

4-methylamino-6-chloro-3-[2-(1-propylbutylidene)hydrazino]pyridazine

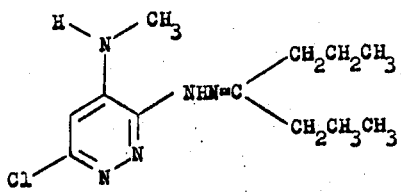

1.928 g. of 4-methylamino-6-chloro-3-hydrazinopyridazine and 7.65 g. of 4-heptanone are dissolved in 170 ml. of methanol and stirred for 6 hours at room temperature. By repeated concentration of the reaction mixture at room temperature a total of 2.46 g. of 4-methylamino-6-chloro-3-[2-(1-propylbutylidene)-hydrazino]-pyridazine; m.p. 94°–96°C. is obtained.

When 4-amino-3-hydrazinopyridazine, 4-methylamino-3-hydrazinopyridazine, 4-isobutylamino-3-hydrazinopyridazine, 5-amino-3-hydrazinopyridazine, 4-amino-6-chloro-3-hydrazinopyridazine, 4-(2-hydroxyethylamino)-6-chloro-3-hydrazinopyridazine, 4-allylamino-6-chloro-3-hydrazinopyridazine, 4-methallylamino-6-chloro-3-hydrazinopyridazine, 4-anilino-6-chloro-3-hydrazinopyridazine, 4-(p-chloroanilino)-6-chloro-3-hydrazinopyridazine, 4-(p-ethylanilino)-6-chloro-3-hydrazinopyridazine, 4-(p-methoxyanilino)-6-chloro-3-hydrazinopyridazine or 4-(α,α,α-trifluoro-p-toluidino)-6-chloro-3-hydrazinopyridazine is used in place of 4-methylamino-6-chloro-3-hydrazinopyridazine in the process of this example, 4-amino-3-[2-(1-propylbutylidene)hydrazino]pyridazine, 4-methylamino-3-[2-(1-propylbutylidene)hydrazino]pyridazine, 4-isobutylamino-3-[2-(1-propylbutylidene)hydrazino]pyridazine, 5-amino-3-[2-(1-propylbutylidene) hydrazino]pyridazine, 4-amino-6-chloro-3-[2-(1-propylbutylidene)hydrazino] pyridazine, 4-(2-hydroxyethylamino)-6-chloro-3-[2-(1-propylbutylidene) hydrazino]pyridazine, 4-allylamino-6-chloro-3-[2-(1-propylbutylidene)-hydrazino]pyridazine, 4-methallylamino-6-chloro-3-[2-(1-propylbutylidene) hydrazino]pyridazine, 4-anilino-6-chloro-3-[2-(1-propylbutylidene) hydrazino]pyridazine, 4-(p-chloroanilino)-6-chloro-3-[2-(1-propylbutylidene)hydrazino]pyridazine, 4-(p-ethylanilino)-6-chloro-3-[2-(1-propylbutylidene)hydrazino]pyridazine, 4-(p-methoxyanilino)-6-chloro-3-[2-(1-propylbutylidene)hydrazino]pyridazine, or 4-(α,α,α-trifluoro-p-toluidino)-6-chloro-3-[2-(1-propylbutylidene)hydrazino]pyridazine, respectively, is obtained.

EXAMPLE 18

4-ethylamino-6-chloro-3-[2-(1-methylbutyliden)hydrazino]pyridazine

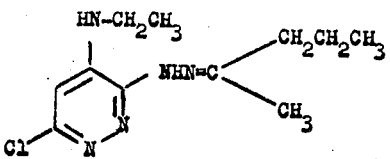

1.5 g. of the 4-ethylamino-6-chloro-3-hydrazino pyridazine and 4.14 g. of 2-pentanone are dissolved in 130 ml. of methanol and maintained at room temperature for 1 hour. The solution is concentrated to about 100 ml. and the produce is precipitated by the addition of 250 ml. of water. The yield of 4-ethylamino-6-chloro-3-[2-(1-methylbutylidene) hydrazino]pyridazine, m.p. 83°–85°C., is 1.65 g.

When allylacetone, benzaldehyde, methylbenzyl ketone or phenyl styryl ketone are substituted for 2-pentanone in the process of this example, 4-ethylamino-6-chloro-3-[2-(2-methylbutene-3-ylidene)hydrazino] pyridazine, 4-ethylamino-6-chloro-3-(2-benzylidenehydrazino)pyridazine, 4-ethylamino-6-chloro-3-[2-(1-methyl-2-phenethylidene)hydrazino]pyridazine or 4-ethylamino-6-chloro-3-[2-(1-phenylcinnamylidene)hydrazino]pyridazine, respectively, is obtained.

EXAMPLE 19

4-amino-6-chloro-3-(2-isopropylidene hydrazino)pyridazine

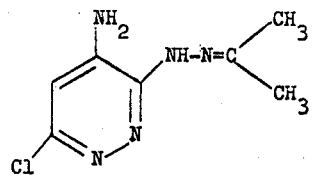

To 5 g of 4-amino-6-chloro-3-hydrazinopyridazine dissolved in 450 ml of methanol, 15 ml of acetone are added and the solution is stirred for about 2 hours at room temperature. The solvent is partially evaporated and the product, 4-amino-6-chloro-3-(2-isopropylidene hydrazino)pyridazine (mp. 158° – 162° C.), is recovered by filtration.

The free base is dissolved in methanol and treated with hydrogen chloride gas at room temperature for about 30 minutes. The methanol is partially removed by evaporation; and the product, 4-amino-6-chloro-3-(2-isopropylidene hydrazino)pyridazine (mp 220° – 227° C.), precipitates.

What is claimed is:
1. A compound of the formula:

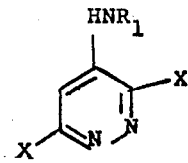

where
each X is the same and represents halo of atomic weight between about 35 to 80, and
$R_1$ represents lower alkenyl, $-(CH_2)_mOH$, wherein m is 2, 3, or 4, or

where
$R_4$ represents hydrogen or halo having an atomic weight of 19 to 36, lower alkyl, lower alkoxy, or trifluoromethyl.

2. A compound having the structure

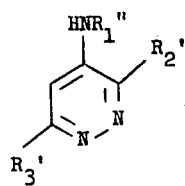

where
$R_1''$ is lower alkenyl and
one of $R_2'$ and $R_3'$ represents hydrazino and the other represents hydrogen or halo having an atomic weight of about 35 to 80 or
a pharmaceutically acceptable acid addition salt thereof, provided that when $R_1''$ is lower alkyl, one of $R_2'$ and $R_3'$ is hydrogen.

3. The compound of claim 2 which is 4-allylamino-6-chloro-3-hydrazinopyridazine.

4. The compound of claim 2 which is 4-methallylamino-6-chloro-3-hydrazinopyridazine.

5. A compound having the structure

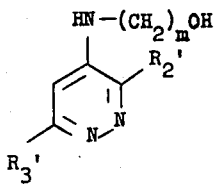

where
m is 2, 3 or 4 and
one of $R_2'$ and $R_3'$ is hydrazino and the other is hydrogen or halo of atomic weight between 35 to 80 or
a pharmaceutically acceptable acid addition salt thereof.

6. The compound of claim 5 which is 4-(2-hydroxyethylamino)-6-chloro-3-hydrazinopyridazine.

7. A compound having the structure

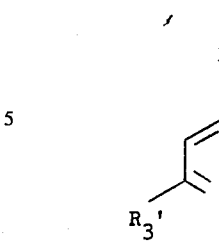

where
one of $R_2'$ and $R_3'$ is hydrazino and the other is hydrogen or halo of atomic weight between 35 to 80, and
$R_4$ is hydrogen; halo having an atomic weight of about 19 to 36; lower alkyl; lower alkoxy or trifluoromethyl or
a pharmaceutically acceptable acid addition salt thereof.

8. The compound of claim 7 which is 4-anilino-6-chloro-3-hydrazinopyridazine.

9. A compound having the structure

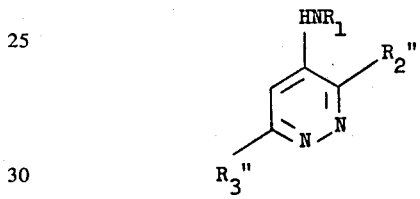

where
one of $R_2''$ and $R_3''$ is hydrogen or halo having an atomic weight of 35 to 80, and the other is

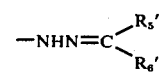

where
$R_5'$ and $R_6'$ each independently represent hydrogen, lower alkyl or lower alkenyl, and
$R_1$ is as defined above or
a pharmaceutically acceptable acid accidion salt thereof.

10. The compound of claim 9 which is 4-methylamino-6-chloro-3-[2-(1-propylbutylidene)hydrazino]pyridazine.

11. The compound of claim 9 which is 4-ethylamino-6-chloro-3-[2-(1-methylbutylidene)hydrazino]pyridazine.

12. The compound of claim 9 which is 4-amino-6-chloro-3-(2-isopropylidene)hydrazine-pyridazine.

13. A compound according to claim 1 which is 3,6-dichloro-4-(2-hydroxyethylamino)pyridazine.

14. A compound according to claim 1 which is 3,6-dichloro-4-methallylaminopyridazine.

15. A compound according to claim 1 which is 3,6-dichloro-4-anilinopyridazine.

16. A compound according to claim 1 which is 3,6-dichloro-4-allylaminopyridazine.

* * * * *